United States Patent [19]

Berg

[11] Patent Number: 5,338,411

[45] Date of Patent: Aug. 16, 1994

[54] SEPARATION OF ETHANOL FROM ISOPROPANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,044

[22] Filed: Jan. 14, 1994

[51] Int. Cl.⁵ .................... B01D 3/36; C07C 29/84
[52] U.S. Cl. .......................... 203/60; 203/58; 203/62; 203/63; 203/68; 203/70; 568/913
[58] Field of Search ............ 203/60, 63, 62, 68, 203/70, 58; 568/913

[56] References Cited

U.S. PATENT DOCUMENTS

| | | | |
|---|---|---|---|
| 2,483,246 | 9/1949 | Stribley | 203/60 |
| 2,487,086 | 11/1949 | Amick et al. | 203/63 |
| 2,512,585 | 6/1950 | Smith | 203/70 |
| 4,710,274 | 12/1987 | Berg et al. | 203/51 |

Primary Examiner—Wilbur Bascomb, Jr.

[57] ABSTRACT

Ethanol is difficult to separate from isopropanol by conventional distillation or rectification because of the proximity of their boiling points. Ethanol can be readily separated from isopropanol by azeotropic distillation. Effective agents are methyl ethyl ketone, cyclopentane and 2-pyrrolidinone.

1 Claim, No Drawings

SEPARATION OF ETHANOL FROM ISOPROPANOL BY AZEOTROPIC DISTILLATION

FIELD OF THE INVENTION

This invention relates to a method for separating ethanol from isopropanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce complex mixtures of oxygenated organic compounds, e.g. the Fischer-Tropsch process. In this mixture, a series of homologous alcohols are often produced. Two of the commonest alcohols in this mixture are ethanol and isopropanol. Ethanol boils at 78.4° C. and isopropanol at 82.4° C. The relative volatility between these two is 1.14 which makes it very difficult to separate them by conventional rectification. Azeotropic distillation would be an attractive method of effecting the separation of ethanol from isopropanol if agents can be found that (1) will create a large apparent relative volatility between ethanol and isopropanol and (2) are easy to recover from ethanol. Table 1 shows the relative volatility required-to obtain 99% purity. With no agent, the relative volatility is 1.14 and 93 actual plates are required. With an agent giving a relative volatility of 1.45, only 34 plates are required.

OBJECTIVE OF THE INVENTION

The object of this invention is to provide a process or method of azeotropic distillation that will enhance the relative volatility of ethanol from isopropanol in their separation in a rectification column. It is a further object of this invention to identify organic compounds which in addition to the above constraints, are stable, can be separated from ethanol and recycled to the azeotrope column with little decomposition.

TABLE 1

Theoretical and Actual Plates Required vs. Relative Volatility for Ethanol - Isopropanol Separation

| Relative Volatility | Theoretical Plates Required At Total Reflux, 99% Purity | Actual Plates Required, 75% Efficiency |
| --- | --- | --- |
| 1.14 | 70 | 93 |
| 1.20 | 50 | 67 |
| 1.25 | 42 | 56 |
| 1.30 | 35 | 47 |
| 1.35 | 31 | 41 |
| 1.45 | 25 | 34 |

SUMMARY OF THE INVENTION

The objects of this invention are to provide a process for separating ethanol from isopropanol which entails the use of certain organic compounds as the agent in azeotropic distillation.

DETAILED DESCRIPTION OF THE INVENTION

I have discovered that certain organic compounds will greatly improve the relative volatility of ethanol to isopropanol and permit the separation of ethanol from isopropanol by rectification when employed as the agent in azeotropic distillation. Table 2 lists the compounds that I have found to be effective. They are methyl formate, ethyl formate, t-butyl methyl ether, isopropyl ether, methyl isopropyl ketone, 2,2-dimethoxy propane, t-amyl methyl ether, methyl propionate 2,3-butanedione, 1,3-dioxolane, 2-pyrrolidinone, propyl formate, acetone, methyl ethyl ketone, hexane, cyclopentane, cyclohexane, hexene-1 and 2,4-dimethyl pentane.

TABLE 2

Effective Azeotropic Distillation Agents For Separating Ethanol From Isopropanol

| Compounds | Relative Volatility |
| --- | --- |
| None | 1.14 |
| Methyl formate | 1.2 |
| t-Butyl methyl ether | 1.2 |
| Isopropyl ether | 1.25 |
| Methyl isopropyl ketone | 1.3 |
| 2,2-Dimeth oxy propane | 1.2 |
| Ethyl formate | 1.35 |
| t-Amyl methyl ether | 1.3 |
| Methyl propionate | 1.35 |
| 2,3-Butanedione | 1.2 |
| 1,3-Dioxolane | 1.4 |
| 2-Pyrrolidinone | 1.45 |
| Propyl formate | 1.25 |
| Acetone | 1.20 |
| Methyl ethyl ketone | 1.45 |
| Hexane | 1.4 |
| Cyclopentane | 1.45 |
| Cyclohexane | 1.35 |
| Hexene-1 | 1.4 |
| 2,4-Dimethyl pentane | 1.45 |

THE USEFULNESS OF THE INVENTION

The usefulness or utility of this invention can be demonstrated by referring to the data presented in Tables 1 and 2. All of the successful agents show that ethanol can be separated from isopropano by means of azeotropic distillation in a rectification column and that the ease of separation as measured by relative volatility is considerable.

WORKING EXAMPLES

EXAMPLE 1

Eighty grams of ethanol, 20 grams of isopropanol and 50 grams of cyclopentane were charged to a vapor-liquid equilibrium still and refluxed for two hours. Analysis indicated a vapor composition 87.3% ethanol, 12.7% isopropanol; a liquid composition of 82.6% ethanol, 17.4% isopropanol. This is a relative volatility of 1.45.

EXAMPLE 2

One hundred and fifty grams of a mixture comprising 50% ethanol and 50% isopropanol and 100 grams of acetone was placed in the stillpot of a 7.3 theoretical plate glass perforated plate rectification column and refluxed for two hours. The overhead composition was 84.8% ethanol, 15.2% isopropanol; the bottoms composition was 58% ethanol, 42% isopropanol which is a relative volatility of 1.21.

I claim:

1. A method for recovering ethanol from a mixture of ethanol and isopropanol which comprises distilling a mixture of ethanol and isopropanol in the presence of an azeotrope forming agent, recovering the ethanol and the azeotrope forming agent as overhead product and obtaining the isopropanol as bottoms product, wherein said azeotrope forming agent consists of one material selected from the group consisting of methyl formate, ethyl formate, t-butyl methyl ether, acetone, and cyclopentane.

* * * * *